US00PP26330P3

(12) United States Plant Patent
Lommerse

(10) Patent No.: US PP26,330 P3
(45) Date of Patent: Jan. 19, 2016

(54) ***DAHLIA* PLANT NAMED 'LODABALVIO'**

(50) Latin Name: ***Dahlia* hybrid**
Varietal Denomination: LODABALVIO

(71) Applicant: Henry Lommerse, Mariahout (NL)

(72) Inventor: Henry Lommerse, Mariahout (NL)

(73) Assignee: Lommerse Holding B.V. (NL)

( * ) Notice: Subject to any disclaimer, the term of this patent is extended or adjusted under 35 U.S.C. 154(b) by 166 days.

(21) Appl. No.: 13/998,286

(22) Filed: Oct. 18, 2013

(65) Prior Publication Data

US 2015/0113691 P1 Apr. 23, 2015

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Anne Grunberg
(74) *Attorney, Agent, or Firm* — Cassandra Bright

(57) ABSTRACT

A new and distinct *Dahlia* cultivar named 'LODABALVIO' is disclosed, characterized by bright violet flower color and full and compact plant growth. The new variety is a *Dahlia*, typically produced as an indoor ornamental plant.

1 Drawing Sheet

Latin name of the genus and species: *Dahlia* hybrid.
Variety denomination: 'LODABALVIO'.

BACKGROUND OF THE INVENTION

This application relates to a new cultivar of *Dahlia* hybrid. The new variety is the product of a planned breeding program. The new variety originated as a seedling from the crossing of the unpatented, proprietary seed parent *Dahlia* '268842' with the unpatented, proprietary pollen parent referred to as *Dahlia* '268857'. The crossing was made by the inventor in his research greenhouse in Mariahout, the Netherlands during July of 2006.

The new variety was first selected by the inventor, Henry Lommerse, a citizen of Netherlands, in July of 2007 at the research greenhouse in Mariahout, the Netherlands. After identifying the new variety as a potentially interesting selection, the inventor continued confidential testing and propagation of 'LODABALVIO', assessing stability of the unique characteristics of this variety.

Asexual reproduction of the new cultivar 'LODABALVIO' was first performed at a commercial laboratory in Mariahout, the Netherlands by vegetative cuttings in October of 2008. Access to all plants was restricted, as plants were kept in a location not open to the public. Through subsequent propagation both by tissue culture and vegetative cuttings, multiple generations have been reproduced, which have shown that the unique features of this cultivar are stable and reproduced true to type.

SUMMARY OF THE INVENTION

The cultivar 'LODABALVIO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LODABALVIO.' These characteristics in combination distinguish 'LODABALVIO' as a new and distinct *Dahlia* cultivar:

1. Unique very bright violet flower color.
2. Compact plant growth.
3. Full, dense plants formed by excellent branching.
4. 4. Flowers held above foliage.

PARENT COMPARISON

Plants of the new cultivar 'LODABALVIO' are similar to the seed parent, *Dahlia* '268842' in most horticultural characteristics. However the new variety, 'LODABALVIO' differs from '268842' in the following characteristics:

1. Violet flower color compared to the purple flower of the seed parent.

Plants of the new cultivar 'LODABALVIO' are similar to the pollen parent, *Dahlia* '268857' in most horticultural characteristics. However the new variety, 'LODABALVIO' differs from '268857' in the following characteristics:

1. Violet flower color compared to the pink flower of the pollen parent.

COMMERCIAL COMPARISON

'LODABALVIO' is similar in most horticultural characteristics to the unpatented commercial variety *Dahlia* 'AZTEC CHIAPAS' in most horticultural characteristics. However the new variety, 'LODABALVIO' differs from 'AZTEC CHIAPAS' in the following characteristics:

1. Flower color is bright violet. Comparator flower color is purple-red.
2. Different flower shape.
3. New variety has a smaller leaf size.
4. New variety has a more compact plant shape.

BRIEF DESCRIPTION OF THE PHOTOGRAPH

The accompanying photograph in FIG. 1 illustrates in full color a typical plant of 'LODABALVIO' grown outdoors in Honselersdijk, the Netherlands. The plant is approximately 14 weeks from rooted cutting in a 3 liter pot.

The photograph was taken in July using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'LODABALVIO' plants grown outdoors in July in Honselersdijk, the Netherlands. The plant is approximately 14 weeks from rooted cutting in a 3 liter pot. Temperatures ranged between 8° C. and 30° C. day and night. No photoperiodic or chemical treatments were given to the plants. During bright Summer conditions, shade was given. Measurements and numerical values represent averages of typical plant types. Botanical classification: *Dahlia* hybrid. 'LODABALVIO'.

PROPAGATION

Time to initiate roots:
- *Summer*.—Approximately 10 days at approximately 20° C.
- *Winter*.—Approximately 15 days at approximately 17° C.

Root description: Roots very fine, heavily branched, moderately fibrous, not fleshy, colored RHS 199D.
Tuber description: No tubers present.

PLANT

Growth habit: Broad spreading-upright, with flowers above foliage.
Pot size of plant described: 3 liter circular.
Height: 24.5 cm. to top of flowering plane. 19.8 cm to top of foliar plane.
Plant spread: 32.7 cm.
Growth rate: Low to moderate.
Length of primary lateral branches: Average 11.4 cm.
Quantity of primary lateral branches: Average 7.
Characteristics of primary lateral branches:
- *Diameter*.—0.5 cm.
- *Color*.—RHS 144A, upper part of branch covered with a thin waxy layer, coloured greyed-green; near RHS 191C and 191D.
- *Texture*.—Smooth, moderately glossy, Upper part of branch covered with a thin waxy layer.
- *Strength*.—Moderately strong.

Internode length: 4.3 cm.

FOLIAGE

Leaf:
- *Arrangement*).—Compound, with an overall ovate shape. Leaflets: 3 . Shape: Ovate, Quantity: Approximately 6 per branch, arranged in 3 pairs. Average Overall Length: 8.4 cm. Average Overall Width: 7.0 cm.

Individual leaf blades:
- *Shape of blade*.—Ovate to elliptic.
- *Apex*.—Apiculate.
- *Base*.—Attenuate.
- *Margin*.—Coarsely serrate.
- *Texture of top surface*.—Glabrous, very slightly glossy.
- *Texture of bottom surface*.—Glabrous.
- *Pubescence*.—No leaf pubescence.
- *Aspect*.—Flat.
- *Color*.—Young foliage upper side: Green; near RHS 143A, base lighter; near RHS 143B. Young foliage under side: Yellow-green; near RHS 146B. Mature foliage upper side: Green; near RHS N137B. Mature foliage under side: Greyed-green; near RHS 191B.
- *Venation*.—Type: Pinnate. Venation color upper side: Yellow-green; near RHS 144A. Venation color under side: Yellow-green; near RHS 147B.
- *Petiole*.—Length: 3.5 cm. Diameter: 0.3 cm. Color: Yellow-green; near RHS 144A. Texture: Glabrous, moderately glossy.
- *Stipule description*.—No stipules present.

FLOWERING CHARACTERISTICS

Natural flowering season: Summer.
Days to flowering from rooted cutting: 65 days.
Inflorescence and flower type and habit: Semi-double, slightly outward in an average angle of 35° (0°=vertical) to near vertical.
Rate of flower opening: 14 to 21 days from bud to fully opened flower.
Flower longevity on plant: Approx. 2 weeks.
Persistent or self-cleaning: Persistent.
Bud:
- *Shape*.—Flattened globular.
- *Length*.—1.1 cm.
- *Diameter*.—1.3 cm.
- *Color*.—Yellow-green; near RHS 144B, top lighter; near RHS N144C.

Flower size:
- *Diameter*.—8.1 cm.
- *Depth*.—6.6 cm.
- *Aspect*.—Slightly outward in an average angle of 35° (0°=vertical).

Petals:
- *Quantity*.—Approx. 76.
- *Arrangement*.—Rotate, in 4 rows.
- *Length*.—3.6 cm.
- *Width*.—2.1 cm.
- *Shape*.—Obovate, strongly concave, base fused.
- *Apex*.—Obtuse.
- *Base*.—Cuneate.
- *Margin*.—Entire.
- *Texture, upper and lower surfaces*.—Glabrous, velvety, matte.
- *Color*.—When opening, upper surface: Purple; near RHS N78A, base dark red-purple; near RHS 59A but darker. When opening, lower surface: Red-purple; near RHS 72A and 72B. Fully opened, upper surface: Purple; near RHS N74A and 74B. Base red-purple; near RHS 60A. Fully opened, lower surface: Red-purple; near RHS N74B and N74C.

Sepals:
- *Quantity*.—8.
- *Length*.—1.2 cm.
- *Width*.—0.6 cm.
- *Shape* (*overall*).—Elliptic.
- *Apex*.—Acute.
- *Base*.—Cuneate.

*Margin*.—Entire.
*Color*.—Green; near RHS 137A.
Peduncles:
*Length*.—7.8 cm.
*Diameter*.—0.35 cm.
*Angle*.—About 0° to the lateral branch (=straight on top of lateral branch), secondary peduncles in an average angle of 10° (0°=vertical).
*Strength*.—Strong.
*Texture*.—Smooth, moderately glossy.
*Color*.—Yellow-green; near RHS 146A, heavily flushed grey-brown; near RHS N199B. Covered with a thin waxy layer, coloured greyed-green; near RHS 191C and 191D.
*Strength*.—Strong.
Fragrance: Very faint.

REPRODUCTIVE ORGANS

Stamens:
*Number*.—Average 20 disc florets per inflorescence. Each disc floret carries an average of 5 stamen.
Anthers:
*Shape*.—Linear.
*Length*.—Approximately 0.5 cm.
*Color*.—Yellow; near RHS 12A.
*Pollen*.—Color: Yellow-orange; near RHS 17A. Quantity: Moderate.
Pistil: Present.
*Number*.—Average: 1.
*Length*.—1.2 cm.
*Style*.—Length: 0.9 cm. Color: Yellow; near RHS 12C.
*Stigma*.—Shape: Cleft (3-parted). Color: RHS Yellow-Orange 17A. Ovary Color: RHS Yellow-Green 145C/D.

OTHER CHARACTERISTICS

Disease resistance: Neither resistance nor susceptibility to the normal diseases found in *Dahlia* has been observed.
Observed temperature tolerance range: −5 degree Celsius to 35 degree Celsius.
Fruit/seed production: No fruits/seeds detected to date.

What is claimed is:

1. A new and distinct cultivar of *Dahlia* plant named 'LODABALVIO' as herein illustrated and described.

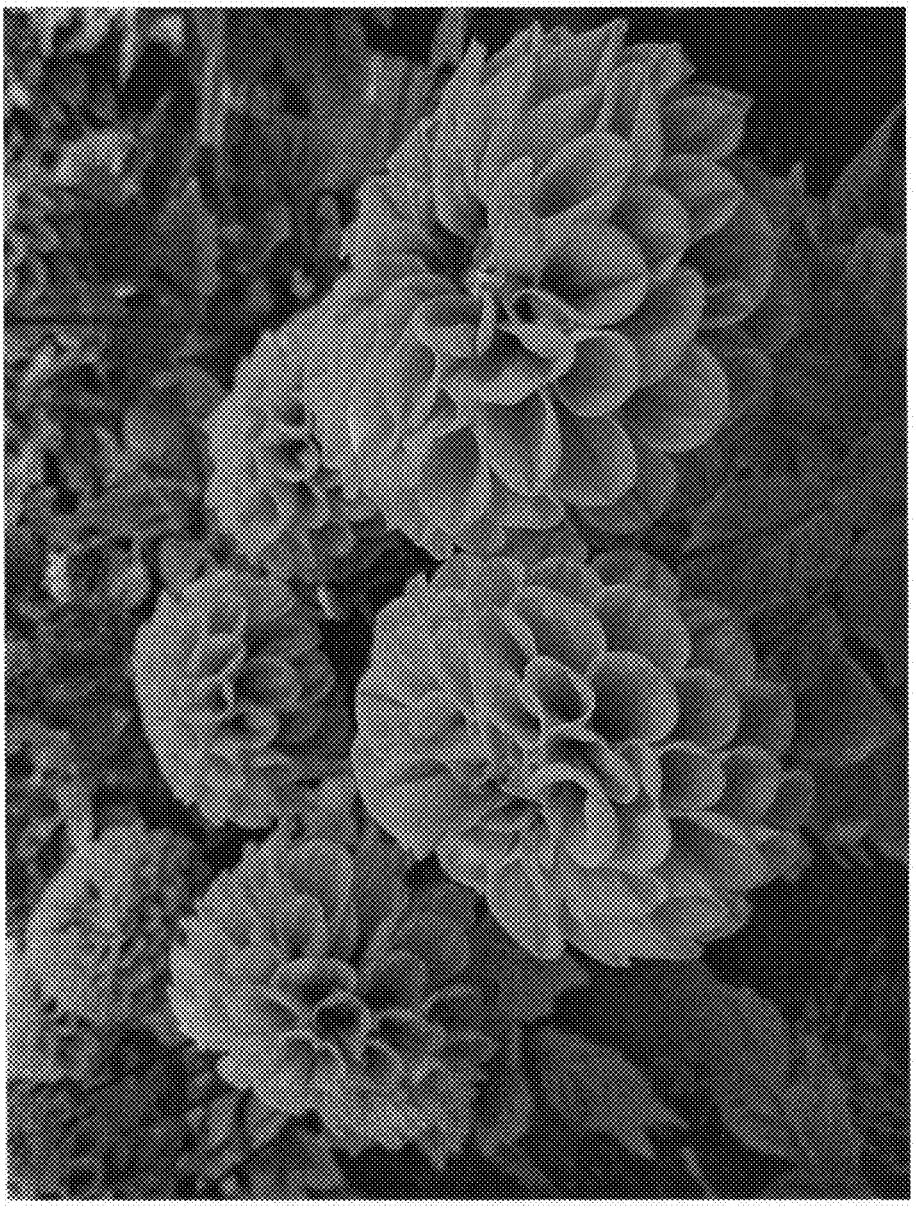

* * * * *